US008823544B2

(12) United States Patent
Mehta

(10) Patent No.: US 8,823,544 B2
(45) Date of Patent: Sep. 2, 2014

(54) METHODS AND SYSTEMS FOR REAL-TIME MONITORING OF ENVIRONMENTS

(75) Inventor: Neelesh B. Mehta, Bangalore (IN)

(73) Assignee: Indian Institute of Science, Karnataka (IN)

( * ) Notice: Subject to any disclaimer, the term of this patent is extended or adjusted under 35 U.S.C. 154(b) by 573 days.

(21) Appl. No.: 13/139,223

(22) PCT Filed: Aug. 14, 2010

(86) PCT No.: PCT/IB2010/002009
§ 371 (c)(1),
(2), (4) Date: Jun. 10, 2011

(87) PCT Pub. No.: WO2011/121387
PCT Pub. Date: Oct. 6, 2011

(65) Prior Publication Data
US 2012/0313791 A1    Dec. 13, 2012

(30) Foreign Application Priority Data
Mar. 30, 2010    (IN) .............................. 882/CHE/2010

(51) Int. Cl.
*G08C 19/16*    (2006.01)
*G01N 21/17*    (2006.01)

(52) U.S. Cl.
CPC ..................................... *G01N 21/17* (2013.01)
USPC .................................................... 340/870.01

(58) Field of Classification Search
USPC ............. 340/870.01, 506, 3.21, 3.41, 870.16, 340/870.17; 702/130, 182, 185
See application file for complete search history.

(56) References Cited

U.S. PATENT DOCUMENTS

| 6,112,164 | A  | * | 8/2000  | Hobson ......................... 702/132 |
| 6,182,022 | B1 | * | 1/2001  | Mayle et al. .................. 702/182 |
| 6,480,809 | B1 | * | 11/2002 | Slaight .......................... 702/186 |
| 6,882,963 | B1 | * | 4/2005  | Slaight .......................... 702/186 |
| 8,183,887 | B2 | * | 5/2012  | Stojanovic et al. ............. 326/87 |

OTHER PUBLICATIONS

International Search Report and Written Opinion prepared by the Australian Patent Office in PCT/IB2010/002009, date of mailing Nov. 30, 2010.
Kulik et al., "Efficient Data Collection and Selective Queries in Sensor Networks", GSN 2006, LNCS 4540, pp. 25-44 (2008).
Arroyo-Valles et al., "Optimal Selective Transmission under Energy Constraints in Sensor Networks", IEEE Transactions on Mobile Computing, vol. 8, No. 11, Nov. 2009.
Qin et al., "Opportunistic Splitting Algorithms for Wireless Networks", in Proc. Infocomm, pp. 1662-1672, 2004.
Shah et al., "Analysis, Insights and Generalization of a Fast Decentralized Relay Selection Mechanism", Apr. 2010.
Vlasov et al., "Electronic Tongue: Chemical Sensor Systems for Analysis of Aquatic Media", Russian Journal of Chemistry, 2008, vol. 12, pp. 2532-2544.

(Continued)

*Primary Examiner* — Phung Nguyen
(74) *Attorney, Agent, or Firm* — Brundidge & Stanger, P.C.

(57) ABSTRACT

Methods and systems for real-time monitoring of environments are disclosed. The methods include receiving a measurement by a sensor unit, and transmitting a signal to a monitoring station if the measurement is approximately between a lower and an upper threshold. Based on a number of signals received, the monitoring station will broadcast a signal indicating to stop transmission of measurements or to update the lower and the upper threshold and continue transmission of measurements. Transmission of measurements may occur during a given time slot.

20 Claims, 7 Drawing Sheets

(56) References Cited

OTHER PUBLICATIONS

Ong, K.G., et al., "A Wireless Sensor Network for Long-term Monitoring of Aquatic Environments: Design and Implementation," Sensor Letters, vol. 2, No. 1 pp. 1-10, American Scientific Publishers (2004).

Shah, V., et al., "Splitting Algorithms for Fast Relay Selection: Generalizations, Analysis, and a Unified View," IEEE Transactions On Wireless Communications, vol. 9, No. 4, pp. 1525-1535 (2010).

* cited by examiner

METHODS AND SYSTEMS FOR REAL-TIME MONITORING OF ENVIRONMENTS

CROSS REFERENCE TO RELATED APPLICATION

The present application claims priority to Indian patent application serial no. 882/CHE/2010 filed on Mar. 30, 2010. The present application is a U.S. National Phase Application pursuant to 35 U.S.C. 371 of International Application No. PCT/IB2010/002009, filed on Aug. 14, 2010, the entire contents of which are herein incorporated by reference.

BACKGROUND

It occurs more often than desired that large Chemical Companies are forced to close plants that have contaminated water in urban cities. When contamination is high, such cases are easily detected and reported. However, it may be difficult to detect leakage of chemical pollutants into an environment at low levels in real-time. Thus, detection of toxic effluent is often only reported when obviously noxious chemicals contaminate drinking water significantly, or when small amounts of chemicals have leaked into the environment over a period of time such that contamination levels have become highly noticeable.

Detection of real-time pollution at early stages may assist with tracking and enforcing pollution guidelines specified by regulatory bodies. History has shown that quiet, unseen, and undetected effluence over extended periods can lead to serious and dramatic public health and environmental crises. Human and environmental damage may continue to occur as a result of slow, low-level leaks of toxic chemicals into waterways. Early detection of pollutants could help corporations and regulatory bodies take corrective action before larger volumes of pollutants are released.

Existing systems for measuring levels of pollution, effluent discharge rate, etc., frequently include an array of sensors deployed in an environment. Each sensor of the array collects data and periodically transmits a measurement. The sensors may detect pollution by making periodic measurements of variables that help detect presence of pollution. Communication links between pairs of sensors and between sensors and a central unit are employed to enable the sensors to communicate their measurements amongst one another. Energy consumption of a sensor is typically highest during data transmission. Sensors are typically battery powered so as to be portable, and thus, once the battery drains out, the sensor can no longer transmit signals and thus becomes ineffective. The periodic transmissions of data measurements thus have a negative impact on the sensor's lifetime and increase the need for routine maintenance.

SUMMARY

In one example aspect, a method of transmitting measurements of a sensor is described. The method includes receiving a measurement by a sensor unit, and during a first time slot, transmitting a signal to a monitoring station if the measurement is approximately between a lower and an upper threshold. The method also includes receiving a broadcast from the monitoring station, and based on the broadcast, updating the lower and the upper threshold for use during a subsequent time slot. The method further includes making a determination whether the updated lower threshold or the updated upper threshold is lower than a minimum value for the lower and upper threshold, and based on the determination, performing a subsequent transmission during the subsequent time slot if the measurement is approximately between the updated lower and the updated upper threshold.

In another aspect, a method of transmitting measurements of a plurality of sensors within an environment is provided. The method comprises each of the plurality of sensors making a measurement, and each of the plurality of sensors transmitting a signal to a monitoring station during a time slot when the measurement of the sensor is approximately between a lower and an upper threshold, such that only sensors with measurements between the lower and the upper threshold transmit a signal to the monitoring station. The method also includes each of the plurality of sensors receiving a broadcast from the monitoring station, and based on the broadcast, each of the plurality of sensors updating the lower and the upper threshold for use during a subsequent time slot. The method further includes each of the plurality of sensors making a determination whether the updated lower threshold or updated upper threshold is lower than a minimum value for the lower and upper threshold, and based on the determination, each of the plurality of sensors performing subsequent transmissions during subsequent time slots if the measurement of the sensor is approximately between the updated lower and the updated upper threshold for the respective subsequent time slot, such that if the updated lower threshold or the updated upper threshold is lower than the minimum value for the lower and upper threshold each of the plurality of sensors performing no subsequent transmissions.

In another example aspect, a computer readable medium having stored therein instructions executable by a computing device to cause the computing device to perform functions is described. The functions include receiving a measurement by a sensor unit, and during a first time slot, transmitting a signal to a monitoring station if the measurement is approximately between a lower and an upper threshold. The functions further include receiving a broadcast from the monitoring station, and based on the broadcast, updating the lower and the upper threshold for use during a subsequent time slot.

In still another example aspect, a sensor is described that includes a sensor unit, a transceiver, and a processing unit. The sensor unit obtains measurements of characteristics of an environment. The transceiver is coupled to the sensor unit and transmits a signal to a monitoring station during a first time slot if the measurement is approximately between a lower and an upper threshold. The transceiver further receives a broadcast from the monitoring station. The processing unit is coupled to the sensor unit and the transceiver and updates the lower and the upper threshold based on the broadcast received from the monitoring station for use during a subsequent time slot. The processing unit further determines if the updated lower threshold or the updated upper threshold is lower than a minimum value for the lower and upper threshold, and if so, the processing unit directs the transceiver to perform no subsequent transmissions.

In yet another example aspect, a monitoring station is described that includes a transceiver and a processing unit. The transceiver receives signals from sensors in an environment. The processing unit is coupled to the transceiver and instructs the transceiver to broadcast a signal to the sensors in the environment based on a number of signals received from the sensors. For example, (i) if no signals are received from sensors during a time slot, a signal indicating to transmit a signal to the monitoring station for measurements of a lower value is broadcast, (ii) if multiple signals are received from sensors during the time slot, broadcasting a signal indicating to transmit a signal to the monitoring station for measurements of a higher value is broadcast, and (iii) if one signal is received from a given sensor during the time slot, broadcasting a signal indicating to end transmission of signals to the monitoring station for the time slot is broadcast.

In still a further example aspect, a method for communicating between sensors in an environment and a monitoring station is described. The sensors obtain measurements of a characteristic of the environment and transmit a signal to the monitoring station if a value of the measurement is between a lower and an upper threshold. The method includes if no signals are received from sensors during a time slot, broadcasting a signal indicating to transmit a signal to the monitoring station for measurements of a lower value. The method also includes if multiple signals are received from sensors during the time slot, broadcasting a signal indicating to transmit a signal to the monitoring station for measurements of a higher value. The method further includes if one signal is received from a given sensor during the time slot, broadcasting a signal indicating to end transmission of signals to the monitoring station for the time slot.

In yet a further example aspect, a system is described that includes a plurality of sensors and a monitoring station. The plurality of sensors are within an environment and obtain measurements of characteristics of the environment. Each of the plurality of sensors transmits during a first time slot a signal if a respective measurement is approximately between a lower and an upper threshold, and each of the plurality of sensors updates the lower and the upper threshold for use during a subsequent time slot based on received broadcasts. The monitoring station receives transmissions from each of the plurality of sensors, and broadcasts a response to the sensors based on a number of transmissions received. For example, (i) if no signals are received from sensors during a time slot, the monitoring station broadcasts a signal indicating to transmit a signal for measurements of a lower value, (ii) if multiple signals are received from sensors during a time slot, the monitoring station broadcasts a signal indicating to transmit a signal for measurements of a higher value, and (iii) if one signal is received from a given sensor during the time slot, the monitoring station broadcasts a signal indicating to end transmission of signals for the time slot.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
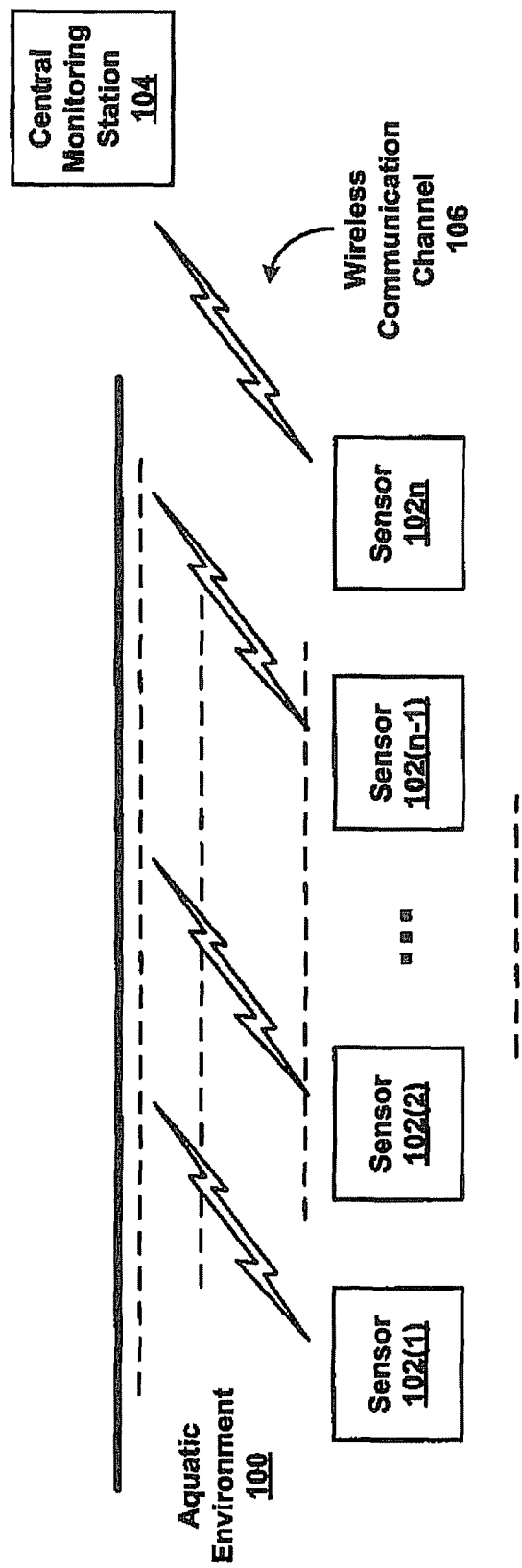
FIG. 1 illustrates an example system for measuring characteristics of an environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and are made part of this disclosure.

Example embodiments describe methods and systems for measuring levels of pollution, effluent discharge rate, etc., and include an array of sensors deployed in an aquatic environment. Each sensor can communicate a measurement to a central monitoring device. The central monitor can raise an alarm or trigger a second-tier of investigative actions if the measurements indicate a cause for alarm, such as a higher than allowed level of effluent discharge, heavy metal concentrations, or lower than acceptable oxygen levels, for example. To monitor the discharge, sensors in the array of sensors may be geographically dispersed. Example embodiments describe methods for reporting sensor measurements to the central monitor. In one aspect, a number of transmissions by the sensors may be optimized to increase a sensor's battery life and to improve a time to detect an undesired change event, for example.

Referring now to the figures, FIG. 1 illustrates an example system for measuring characteristics of an environment. FIG. 1 illustrates an aquatic environment 100 in which sensors 102(1)-102(n) are positioned to measure various aspects and characteristics of the environment. For example, the sensors may measure levels of pollution and effluent discharge rates. Types of pollution to be monitored include levels of pH, oil pollution, levels of oxygen, or any other toxins or indicators of pollution, for example. Any number or type of sensors may be used within the aquatic environment 100, for example. In addition, although FIG. 1 indicates that the environment is an aquatic environment, any type of environment may be monitored, and thus, the number or type of sensor may depend on the type of environment being monitored.

The sensors 102(1)-102(n) may communicate measurements and readings to a central monitoring station 104 via a wireless communication channel 106. Any type of wireless communication protocol may operate over the wireless communication channel 106. For example, the wireless communication protocol that operates over the wireless communication channel 106 may be a wireless protocol for a cellular network.

Alternatively, the sensors 102(1)-102(n) may communicate measurements and readings to the central monitoring station 104 via a wired connection.

The central monitoring station 104 receives the measurements and readings from the sensors 102(1)-102(n) and makes a determination as to a level of pollution of the aquatic environment 100. More monitoring stations may be included within the aquatic environment 100 to receive measurements from the sensors 102(1)-102(n), and to make determinations as to levels of pollution in a particular area, for example. The central monitoring station 104 may thus communicate received measurements from the sensors 102(1)-102(n) to other monitoring stations to further determine levels of pollution in the aquatic environment 100. In addition, the central monitoring station 104 may or may not be positioned centrally within the environment, and thus, the term central does not necessarily indicate position or relation of the central monitoring station 104 to the sensors 102(1)-102(n), for example.

The number of sensors 102(1)-102(n) and central monitoring stations, and type of communication between the sensors 102(1)-102(n) and central monitoring stations may vary according to a specific aquatic environment, or according to a type of pollution or characteristic of the environment being monitored. Furthermore, although FIG. 1 is described in relation to an aquatic environment, those of ordinary skill in the art will understand that the particular arrangement of sensors and monitoring stations may be used in any type of environment to monitor any number of characteristics of the environment. For example, systems and methods described herein may be implemented in many different types of environments including aquatic environments, and may be implemented to monitor many different characteristics such as overall quality monitoring or structural health monitoring, for example. In addition, the sensors 102(1)-102(n) may be arranged in any type of network or configuration, such as a distributed sensor network or a multiple sensor network.

Figure 2:
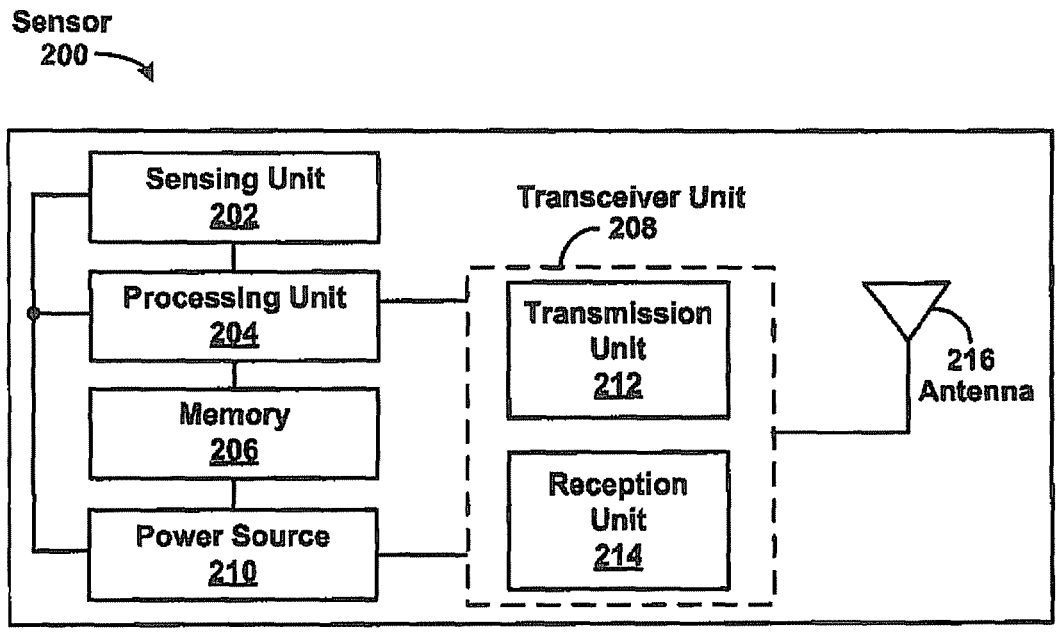
FIG. 2 illustrates a block diagram of an example sensor.

FIG. 2 illustrates a block diagram of an example sensor 200. The sensor 200 includes a sensing unit 202 coupled to a processing unit 204. The processing unit 204 couples to memory 206 and a transceiver unit 208. A power source 210 couples to each of the sensing unit 202, the processing unit 204, the memory 206, and the transceiver unit 208 to provide power to each unit.

The sensing unit 202 may be a hardware device that produces measurable responses to a change in a physical condition, such as temperature or pressure. The sensing unit 202 senses or measures physical data of an area to be monitored. The sensing unit 202 may be a passive sensing unit that senses data without manipulating the environment by active probing, and may or may not have a well-defined notion of direction of measurement. Alternatively, the sensing unit 202 may actively probe the environment, for example, using sonar, radar or seismic technology. The sensing unit 202 may measure or detect any kind of change in an area, and examples of types of sensing units include thermal sensors, pressure sensors, humidity sensors, chemical sensors including oxygen sensors and carbon monoxide detectors, light or photodetector sensors, infra, radiation sensors including a Geiger counter, acoustic or sound sensors including microphones and seismometers, motion sensors, orientation sensors including gyroscopes, and distance or proximity sensors. Any combination of sensors may be used as well depending on a characteristic of an environment being monitored.

The sensing unit 202 may output a continual analog signal that can be digitized by an analog-to-digital converter (not shown). The sensing unit 202 has a certain area of coverage for which the sensing unit 202 can reliably and accurately report a particular aspect that the sensing unit 202 is observing. For example, the sensing unit 202 may be able to detect occurrences over a circle having about a 10 foot radius for some occurrences, or over a circle having about a 1 mile radius for other occurrences. Although only one sensing unit 202 is shown, the sensor 200 may include multiple sensing units, and each sensing unit may or may not monitor or detect the same type of occurrences, for example.

The processing unit 204 may process data and control functionality of components in the sensor 200. The processing unit 204 may be embodied as a processor that accesses the memory 206 to execute software functions stored therein. One skilled in the art of computer systems design will understand that the example embodiments are not limited to any particular class or model of processor. The processing unit 204 may operate according to an operating system, which may be any suitable commercially available embedded or disk-based operating system, or any proprietary operating system. Further, the processing unit 204 may comprise one or more smaller central processing units, including, for example, a programmable digital signal processing engine or may also be implemented as a single application specific integrated circuit (ASIC) to improve speed and to economize space. In general, it should be understood that the processing unit 204 could include hardware objects developed using integrated circuit development technologies, or yet via some other methods, or the combination of hardware and software objects that could be ordered, parameterized, and connected in a software environment to implement different functions described herein. Also, the hardware objects could communicate using electrical signals, with states of the signals representing different data.

The memory 206 may store information such as previously transmitted or received signals, for example. The memory may include random access memory (RAM), flash memory or long term storage, such as read only memory (ROM) or magnetic disks, for example.

The processing unit 204 may receive measurements from the sensing unit 202 and determine whether to transmit the measurement to a central monitoring station via the transceiver unit 208 based on a value of the measurement, for example. The transceiver unit 208 includes a transmission unit 212, a reception unit 214, and an antenna 216. The transceiver unit 208 may operate in different modes including transmit, receive, idle, and sleep, for example. If the transceiver unit 208 is not transmitting or receiving, then the transceiver unit 304 may be placed in sleep mode to conserve power, or idle mode. The transceiver unit 208 may transmit and receive signals simultaneously using the transmission unit 212 and the reception unit 214.

The power source 210 couples to each of the sensing unit 202, the processing unit 204, the memory 206, and the transceiver unit 208 to provide power to each unit. The power source 210 may be an independent power source such as a battery or a solar power source, or the sensor 200 may be connected to other types of conventional power sources.

The processing unit 204 will receive measurements from the sensing unit 202 and determine whether to transmit the measurements based on a value of the measurement compared to threshold values that may be received from a central monitoring station, for example. By limiting transmissions of measurements, the sensor 200 may conserve power of the power source 210.

Figure 3:
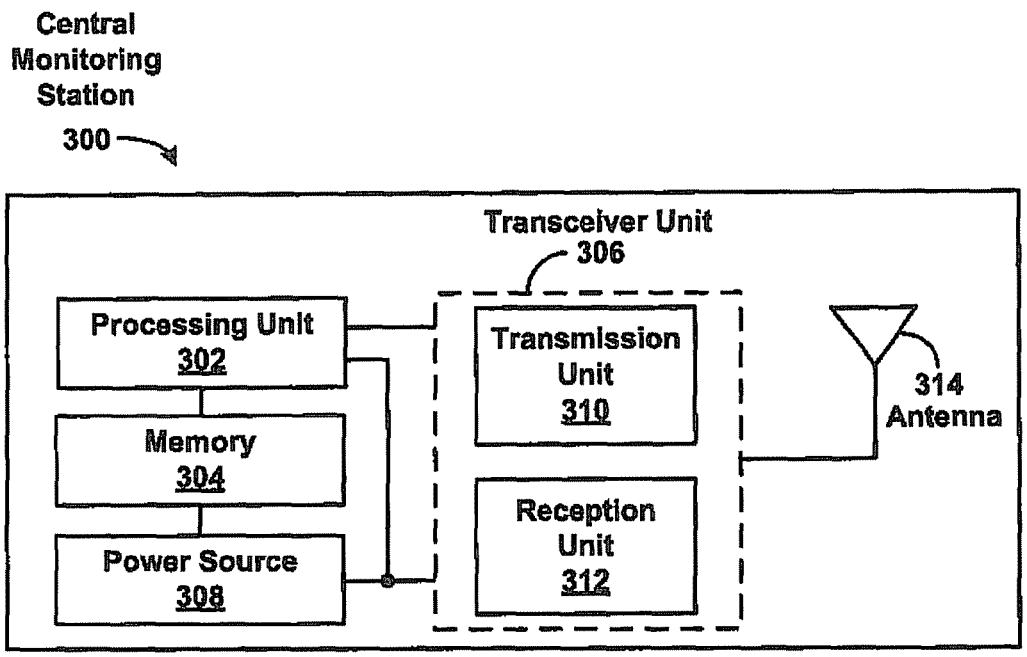
FIG. 3 illustrates a block diagram of an example central monitoring station.

FIG. 3 illustrates a block diagram of an example central monitoring station 300. The central monitoring station 300 includes a processing unit 302 coupled to memory 304 and a transceiver unit 306. A power source 308 couples to each of the processing unit 302, the memory 304, and the transceiver unit 306 to provide power to each unit.

The processing unit 302 may process data and control functionality of components in the central monitoring station 302. The processing unit 302 may be embodied as a processor that accesses the memory 304 to execute software functions stored therein. The processing unit 302 may operate according to an operating system, which may be any suitable commercially available embedded or disk-based operating system, or any proprietary operating system. Further, the processing unit 302 may comprise one or more smaller central processing units, for example. The memory 304 may store information such as previously transmitted or received signals, for example. The memory may include random access memory (RAM), flash memory or long term storage, such as read only memory (ROM) or magnetic disks, for example.

The processing unit 302 may receive measurements from sensors via the transceiver unit 306, for example. The transceiver unit 306 includes a transmission unit 310, a reception unit 312, and an antenna 314. The transceiver unit 306 may operate according to any type of wireless communication protocol.

The power source 308 couples to each of the processing unit 302, the memory 304, and the transceiver unit 306 to provide power to each unit. The power source 308 may be an independent power source such as a battery or a solar power source, or the central monitoring station 300 may be connected to other types of conventional power sources.

The processing unit 302 may receive measurements from sensors and identify a highest measurement level of pollution across all sensors, for example. Based on received measurements, the processing unit 302 may signal an alarm, or broadcast a return signal to the sensors requesting the sensors to modify thresholds for determining when to transmit measurements, for example.

In example embodiments, a method for communicating between sensors and the central monitoring station 300 is provided. For example, instead of each sensor sequentially transmitting a measurement or reading to the central monitoring station 300, the sensors decision to transmit a measurement or reading is based on a magnitude of the current reading. A highest reading level of pollution across all sensors may be detected with few transmissions, and if this reading is lower than a threshold, then this implies that no other sensor has a higher reading. Therefore, the central monitoring station 300 may not be required to take any further action. However, when the highest reading is higher than the threshold, the central monitoring station 300 can takes appropriate secondary action, which may include raising an alarm or inquiring with each sensor about what is being measured, sending out a monitoring crew, etc.

Figure 4:
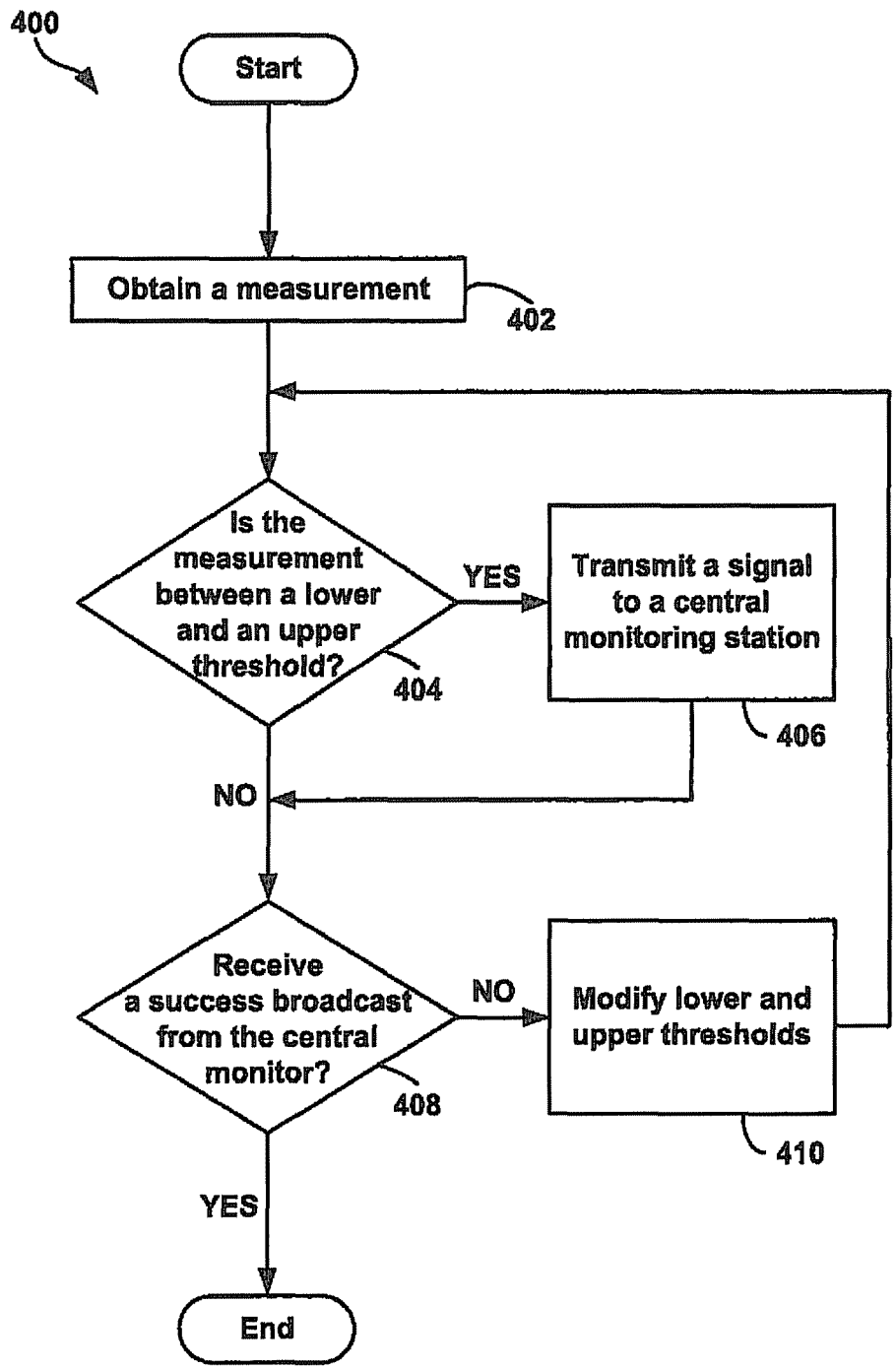
FIG. 4 is a flowchart that depicts example steps of a method for communicating between sensors and a central monitoring station.

FIG. 4 is a flowchart that depicts example steps of a method for communicating between sensors and a central monitoring station. It should be understood that the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. In addition, each block may represent circuitry that is wired to perform the specific logical functions in the process. Alternative implementations are included within the scope of the example embodiments of the present application in which functions may be executed out of order from that shown or discussed, including substantially concurrent or in reverse order, depending on the functionality involved, as would be understood by those reasonably skilled in the art.

Initially, as shown at block 402, a sensor may obtain a measurement. The sensor may measure any number of characteristics about an environment, and the measurement may be in many different forms. For example, the measurement may be a magnitude or level of oxygen in water, or a binary indication as to whether the level of oxygen in the water is above or below a threshold.

If the measurement is between a lower and an upper threshold, the sensor will transmit a signal to the central monitoring station, as shown at blocks 404 and 406. For example, the magnitude of the measurement may be within (or about within) a predefined lower and upper threshold range, and thus, the sensor will transmit a signal to the central monitoring station. The signal may indicate a value or magnitude of the measurement reading, or may simply indicate that the measurement reading is within the lower and upper threshold range (e.g., a binary value of yes or no), for example. The signal may include other information as well, such as a location of the sensor transmitting the signal, information relating to past measurements, information indicating a change in a measurement, etc.

If the measurement is not between the lower and upper threshold, the sensor does not transmit a signal to the central monitoring station. Subsequently, if the sensor receives a success broadcast from the central monitoring station, as shown at block 408, then the method ends. A success broadcast may indicate that the central monitoring station has identified a highest reading from a given sensor, and thus, the central monitoring station can take secondary action, if needed.

Alternatively, if no success broadcast is received from the central monitoring station, then the sensor modifies the lower and/or the upper threshold values, as shown at block 410, and determines if the measurement now falls within the modified threshold range. For example, if no success broadcast is received at the sensor, the sensor may determine that the central monitoring station has not located the highest reading, or that the central monitoring station has received too many readings, and thus, the sensor may raise or lower the threshold values. In one embodiment, the central monitoring station may broadcast a signal to the sensor indicating whether to raise or lower the threshold values (discussed more fully below).

The method described in FIG. 4 may be performed by a group of sensors within an environment, such as the sensors shown in FIG. 1, to enable the central monitoring station to identify a sensor that has a highest (e.g., a worst) reading, for example. In other instances, depending on a characteristic being measured, the method enables the central monitoring station to identify a sensor that has a lowest reading.

The lower (minimum) and upper (maximum) threshold values may also depend on a characteristic being measured, and may also be unbounded. Decisions to transmit or not are made individually by each sensor at a beginning of a time slot. For example, one iteration of the method of FIG. 4 may be performed in one time slot, and each subsequent iteration may be performed over a subsequent time slot, for example. The time slot may be of a length so as to enable transmission of signals by sensors, and a feedback broadcast by the central monitoring station. Depending on a length of data packets associated with these transmissions, a minimum duration of a time slot length may be determined.

Figure 5:
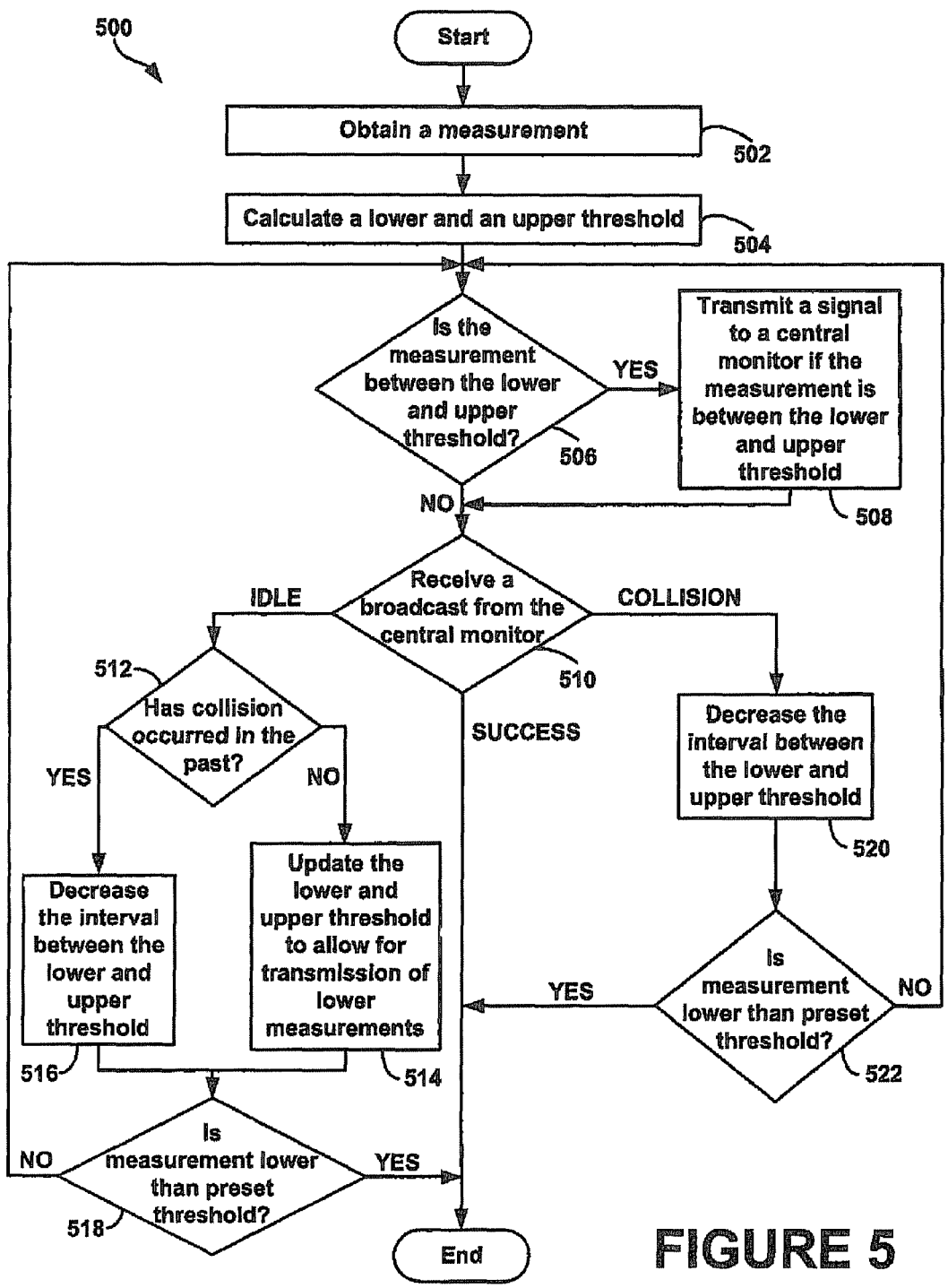
FIG. 5 is another flowchart that depicts example steps of communicating between sensors and a central monitoring station.

FIG. 5 is another flowchart that depicts example steps of communicating between sensors and a central monitoring station. As with the flowchart of FIG. 4, each block may represent a module, a segment, or a portion of program code, which includes one or more instructions executable by a processor for implementing specific logical functions or steps in the process. In addition, each block may represent circuitry that is wired to perform the specific logical functions in the process.

The method of FIG. 5 may be performed by each sensor within an environment, for example. Initially, as shown at block 502, each sensor will obtain a measurement. Measurements may be obtained at a beginning of a time slot, and the method of FIG. 5 may be performed over one time slot, for example.

All sensors may normalize their measurements so that the measurements lie between 0 and 1 uniformly, for example. As one example, if $F_M(x)$ denotes a probability that the measurement value of a sensor is less than x, normalization may be performed by having sensors operate according to $Y=F_M(m)$ instead of m. Since an output of the function is a probability value, the output will lie between 0 and 1. Furthermore, $F_M(m)$ is monotonically increasing in x, i.e., as m increases, $F_M(m)$ increases. Therefore, choosing a sensor with a largest value of m is equivalent to choosing a sensor with a largest value of $F_M(m)$, for example.

Let $H_L(k)$ and $H_H(k)$ denote lower and upper thresholds in a time slot k. A sensor transmits in slot k if the sensor's metric (or measurement), $u_1$, lies between $H_L(k)$ and $H_H(k)$; otherwise, the sensor remains quiet. Thus, as shown at block 504, at the beginning of a slot k, each sensor (independently) calculates two thresholds $H_L(k)$ and $H_H(k)$.

In the first slot, parameters are initialized as follows:

$$H_L(k) = \left(1 - \frac{1}{n}\right)$$ Equation (1)

$$H_H(k) = 1$$ Equation (2)

where the number of sensors is n.

The sensor will transmit with power P to the central monitoring station if the sensor's reading μ satisfies $H_L(k) < \mu < H_H(k)$, as shown at blocks 506 and 508.

Next, as shown at block 510, at the end of each slot, each sensor will receive a broadcast from the central monitoring station. The broadcast may indicate one of the following three example outcomes: i) idle if no sensor transmitted, ii) success if exactly one sensor transmitted, or iii) collision if multiple sensors transmitted. An idle message may indicate that no sensor transmitted a signal, or alternatively, may indicate that less than a satisfactory number of sensors transmitted signals, for example. In addition, a collision message may indicate that more than a desired amount of signals received, for example.

In the case of the outcome being a success, the algorithm terminates. For example, if exactly one sensor transmitted a measurement, then the sensor with the highest measurement has been found. In an alternate example, if one or a small number of sensors transmitted a signal, then a group of sensors with the highest measurements has been found. Once success has been determined, the sensors may receive a signal indicating to terminate the algorithm, and then the sensors may obtain a new measurement at the next subsequent time slot and repeat the method of FIG. 5. Alternatively, the sensors may obtain new measurements upon receiving a signal requesting to do so.

If no success is determined, based on an idle or collision feedback message, the upper and lower thresholds are updated based on the outcome of the previous slot. For example, if the sensor received an idle message (e.g., indicating that the slot was idle and no sensors transmitted a measurement because no sensor recorded a measurement between the lower and upper threshold values), and no collision has occurred in the past, the sensor updates the lower and upper thresholds to allow for transmission of lower measurements, as shown at blocks 512 and 514. For example, if feedback of the kth slot is idle and no collision has occurred thus far, then the lower threshold $H_L(k)$ and the upper threshold $H_H(k)$ may be updated as follows:

$$H_H(k+1) = H_L(k)$$ Equation (3)

$$H_L(k+1) = \left(1 - \frac{(k+1)}{n}\right)$$ Equation (4)

Thus, $H_L(k)$ and $H_H(k)$ are each decreased, and the difference between them remains constant (or substantially constant). Lower magnitude readings may thus be transmitted by the sensors. For n=10 sensors, values of the lower and the upper threshold values may be as shown below in Table 1.

TABLE 1

| k | $H_L(k)$ | $H_H(k)$ |
|---|---|---|
| Initial, k = 0 | 0.9 | 1 |
| 1 | 0.8 | 0.9 |
| 2 | 0.7 | 0.8 |
| 3 | 0.6 | 0.7 |
| 4 | 0.5 | 0.6 |
| 5 | 0.4 | 0.5 |

If the sensor received an idle message and a collision has occurred in the past, the sensor decreases the interval between the previous lower and upper threshold by changing values of both the upper and lower threshold, as shown at block 516. For example, the lower threshold $H_L(k)$ and the upper threshold $H_H(k)$ may be updated as follows:

$$H_H(k+1) = H_L(k)$$ Equation (5)

$$H_L(k+1) = H_L(k) - \frac{(H_H(k) - H_L(k))}{2}$$ Equation (6)

The lower threshold will remain less than the upper threshold, and the lower and upper threshold values will be updated as shown in Equations (5)-(6) after a collision has occurred. For n=10 sensors, example values of the lower and upper thresholds are shown in Table 2 below. This example assumes that a collision has occurred during the first slot (k=0), in which case the new thresholds will become 0.95 and 1.0 for k=1, and that an idle condition occurs at k=1, in which case the thresholds become 0.925 and 0.95 for k=2. Thereafter, the example is for the case in which an idle condition occurs for k≥2.

TABLE 2

| k | $H_L(k)$ | $H_H(k)$ | Outcome |
|---|---|---|---|
| Initial, k = 0 | 0.9 | 1 | Collision |
| 1 | 0.95 | 1 | Idle |
| 2 | 0.925 | 0.95 | Idle |
| 3 | 0.9125 | 0.925 | Idle |
| 4 | 0.90625 | 0.9125 | — |

After updating the lower and the upper threshold values (either as shown in Equations (3)-(4) or Equations (5)-(6)), if the measurement is lower than a preset threshold or preset minimum value (such as, for example, about 0.5 to about 0.8), then the algorithm ends, as shown at block 518. This is because no sensor has a reading greater than a predefined threshold value, and thus, no sensor has identified any problems in the environment, for example. If the measurement is not lower than the preset threshold, the method of FIG. 5 repeats at the next time slot. In an alternate example, after obtaining the measurement, at block 502, it may be determined if the measurement is lower than the preset threshold, and if so, the algorithm ends at that time. The preset minimum value may be set to other values as well, depending on information that is being measured. A value of the preset minimum may determine how quickly the algorithm ends, so that for higher preset minimums, the algorithm ends more quickly.

In still another alternate embodiment, if after updating the lower and the upper threshold values, the lower or the upper threshold value is lower than the preset threshold or preset minimum value for the lower and upper threshold, then the algorithm may end. In this manner, it can be established that when the lower and/or upper threshold is lower than a minimum value for the lower and upper threshold, then no measurement may be of any danger, and thus, it is unnecessary to continue searching to identify the sensor with a highest reading, for example. This may end the algorithm more quickly to save power and processor resources, for example.

Still further, the preset minimum value may be updated with time as well. The preset minimum operates to stop the algorithm when the search thresholds decrease below the minimum, or pre-specified "no danger" sensor reading values. Based on received sensor readings, the "no danger" value may be increased to stop the algorithm more quickly. For example, if over time, a small number or no sensor readings fall within the search thresholds, the preset minimum may be adjusted to stop the algorithm more quickly in the future so as to preserve power and processing availability since the environment has tested successfully in the past.

If the sensor received a collision message (e.g., indicating that multiple sensors transmitted), the sensor recursively decreases the interval between the previous lower and upper threshold until the algorithm terminates with a success, as shown at block 520. For example, the lower threshold may be iteratively increased while holding the upper threshold constant (or substantially constant). The lower threshold $H_L(k)$ and the upper threshold $H_H(k)$ may be updated as follows:

$$H_L(k+1) = \frac{(H_L(k) + H_H(k))}{2} \quad \text{Equation (7)}$$

$$H_H(k+1) = H_H(k) \quad \text{Equation (8)}$$

Thus, $H_L(k)$ can be increased while $H_H(k)$ remains constant, and the difference between the $H_L(k)$ and $H_H(k)$ is decreased. For n=10 sensors, example values of the lower and upper threshold are shown below in Table 3.

TABLE 3

| k | $H_L(k)$ | $H_H(k)$ | Outcome |
|---|---|---|---|
| Initial, k = 0 | 0.9 | 1 | Collision |
| 1 | 0.95 | 1 | Collision |
| 2 | 0.975 | 1 | Collision |
| 3 | 0.9875 | 1 | Collision |
| 4 | 0.99375 | 1 | Collision |
| 5 | 0.996875 | 1 | — |

The algorithm can terminate if the measurement or if the updated lower or updated upper threshold is lower than a preset threshold, as shown at block 522. If not, the method of FIG. 5 repeats at the next time slot.

The method in FIG. 5 may not require all sensors to transmit. For example, only sensors that have information of interest, i.e., with high measurements or readings, will transmit. Therefore, a number of transmissions from the sensors is reduced. For example, instead of each sensor transmitting periodically, only sensors with readings that meet thresholds or that are within a range of thresholds will transmit. Moreover, once thresholds are updated and a higher reading is detected, sensors with lower readings will not need to transmit. For example, with 100 sensors in an aquatic environment, an average number of transmissions using the method of FIG. 5 has been found to be about 5. Thus, only about 5% of the original number of transmissions is required.

Because a number of transmissions from the sensors is reduced, energy consumption by the sensors is also reduced by the reduction in radio transmission. This, in turn, helps increase battery life of each sensor, which prolongs periods over which a network can be operated without requiring routine maintenance due to battery replacement.

Figure 6:
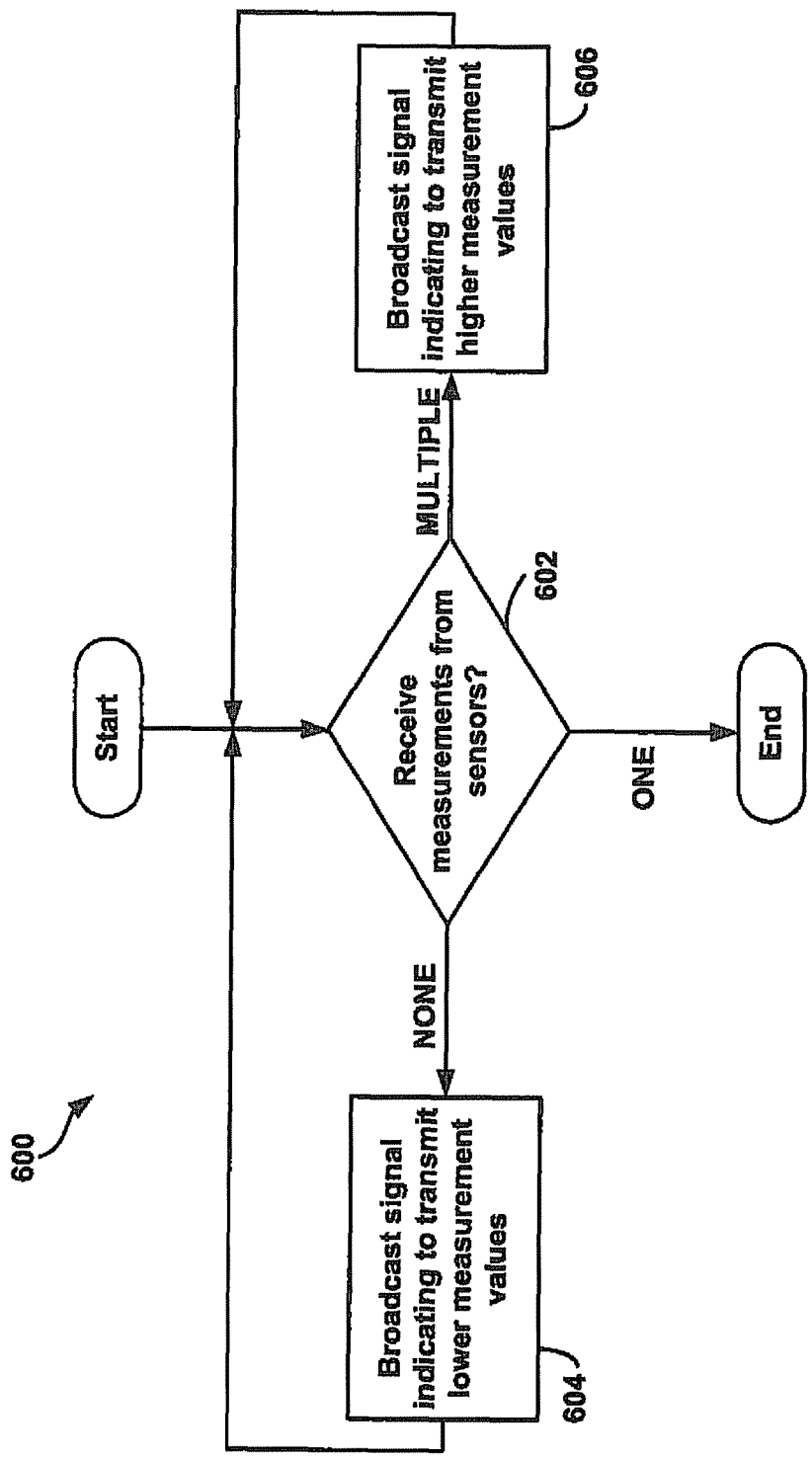
FIG. 6 is another flowchart that depicts example steps of communicating between sensors and a central monitoring station.

FIG. 6 is another flowchart that depicts example steps of communicating between sensors and a central monitoring station. As with the flowcharts of FIGS. 4 and 5, each block may represent a module, a segment, or a portion of program code, which includes one or more instructions executable by a processor for implementing specific logical functions or steps in the process. In addition, each block may represent circuitry that is wired to perform the specific logical functions in the process.

The method of FIG. 6 may be performed by a central monitoring station, such as the central monitoring station 104 in FIG. 1. The method may be performed to locate or identify a sensor that has a highest (or lowest) sensor reading or measurement in an area.

The central monitoring station will monitor received signals from sensors, and based on a number of received signals, the central monitoring station may take secondary action, as shown at block 602. If during a monitoring time slot, the central monitoring station does not receive any signals from sensors (or does not receive a satisfactory number of signals to make an assessment of the quality of the environment), the central monitoring station may broadcast a signal to all sensors indicating to transmit lower measurement values, or simply indicating to those sensors with lower measurement values to transmit, as shown at block 604. For example, if no signals are received, this may indicate that no sensor made a reading that was within a lower and upper threshold range, and thus, no reading qualified to be transmitted to the central monitoring station. Alternatively, if no signals are received, this may indicate that no sensor made a reading of a high enough value so as to trigger a transmission to the central monitoring station. Thus, the central monitoring station may instruct the sensors (through a broadcast, for example) to lower a threshold for determining whether to transmit a signal so that lower readings may be transmitted. When no signals are received, default values of the thresholds for a qualifying reading were set too high, and thus, the central monitoring station will instruct the sensors to lower the thresholds, for example.

Still alternatively, the monitoring station may perform step 602 if less than a satisfactory number of sensors transmitted signals (rather than if no sensors transmitted signals). For example, based on a characteristic being monitored by the sensors, a given number of transmissions may be needed to make an assessment of the quality of the environment.

If the central monitoring station receives multiple signals, the central monitoring station may broadcast a signal indicating to transmit higher measurement values, as shown at block 606. For example, if many signals are received, the central monitoring station will attempt to identify a sensor that records the highest reading (or worst condition) by raising the threshold values used by sensors to determine whether to transmit a signal.

A number of signals that need to be received to trigger step 606 may vary. For example, if the method 600 is performed to identify the sensor with the highest reading, then step 606 may be performed if two or more signals are received. However, if the method 600 is performed to identify a small area that may be polluted, and then step 606 may be performed only if 10 or more signals are received so as to filter the number of signals (e.g., number of sensors transmitting) down to about 10, for example.

If multiple signals are received, the central monitoring station may declare that a collision has occurred. When a collision occurs, the central monitoring station may not be able to decode what was transmitted by any of the transmitting sensors if the signals interfere with each other. The monitor may declare that a collision has occurred when more than a desired amount of signals are received, for example. The central monitor can determine that a collision has occurred, for example, by identifying an increase in received signal power during a time slot k.

As mentioned, the method 600 may also be performed to identify or locate a sensor with a lowest reading, and if so, steps 604 and 606 may be switched so that if no signals are received, the central monitoring station may transmit a signal indicating to transmit higher measurement values, and if multiple signals are received, the central monitoring station may transmit a signal indicating to transmit lower measurement values, for example.

The steps 604 and 606 may be performed in response to receiving or not receiving signals from sensors during a given time slot. Further, the steps 604 and 606 may be repeated during each subsequent time slot until a success is determined, such as, for example, until one signal is received from the sensors. Once a successful result is received, the central monitoring station may indicate to the sensors when to obtain a new measurement and to begin a new sequence of transmissions.

Success may be determined in other ways as well. For example, if one or a small number of sensors transmitted signals, then a success may be determined. A small number of sensors may be between 2-10 or other values based on a total number of sensors that are in the environment. For example, if the environment includes 1000 sensors, then a success may be determined when 50 or less sensors transmit a signal, so that the 50 sensors with the highest readings have been identified. The number of sensors that transmitted may be inferred, for example, from the receive signal power as measured by the monitoring station.

Still alternatively, a success may be determined if a percentage of sensors have transmitted, such as only about 2% to about 5% of the sensors in the environment. The number of sensors or determination of success thus may depend on a number of sensors in the environment, and also may depend on a characteristic being monitored and a number of measurements needed to make an assessment of the characteristic in the environment. Thus, as still another example, a success may be determined when a number of sensors below a threshold number have transmitted.

The methods presented in FIG. 6 may filter out sensor signals so as to eventually receive a signal from only the sensor whose measurement is the highest or lowest, for example. Thus, when the central monitoring station receives only one signal, the central monitoring station may determine that the sensor from which the signal was transmitted has the highest measurement, for example. In this manner, the method may be used for monitoring distributed sensor networks.

Figure 7:
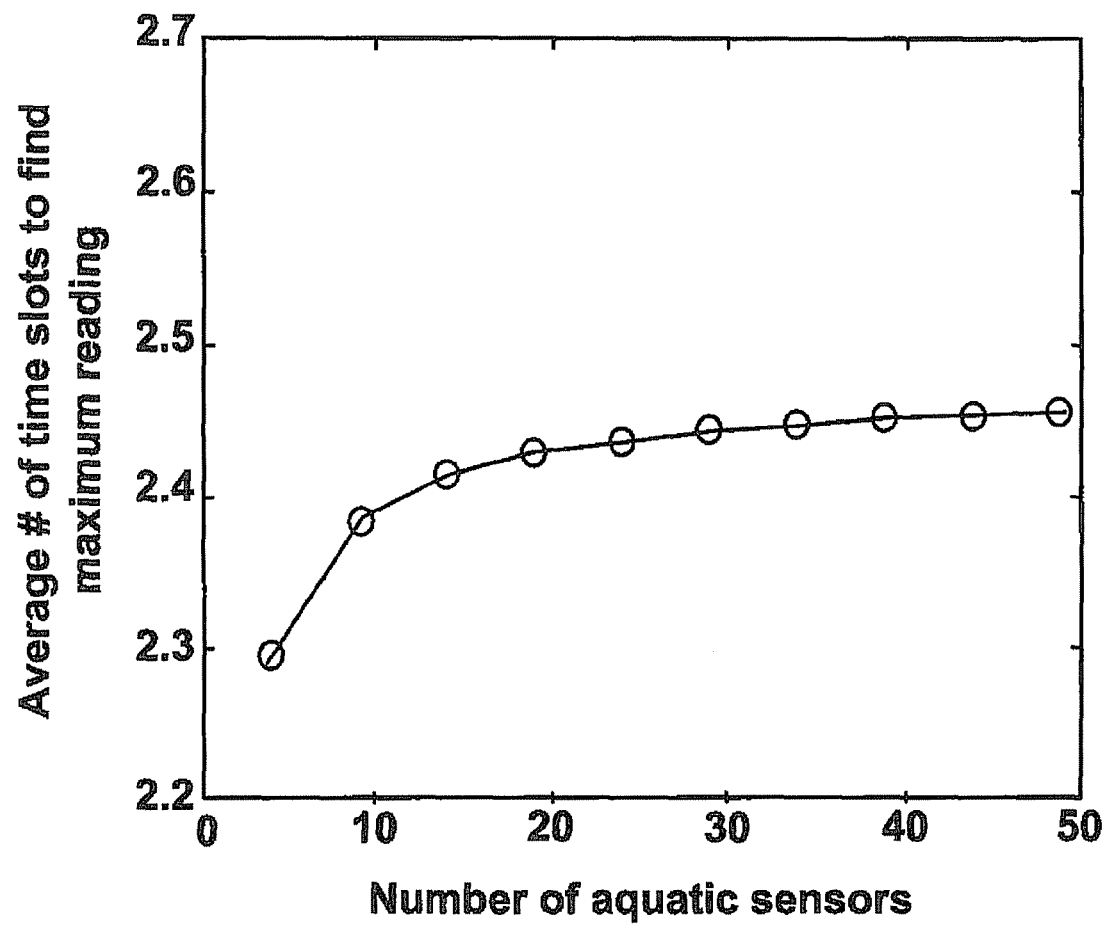
FIG. 7 is an example graph of simulations performed to determine time slots required to identify a highest measurement.

FIG. 7 is an example graph of simulations performed to estimate how many time slots were required to identify a highest measurement. The plot illustrates an average number of time slots required to find a sensor with a highest reading as a function of a total number of sensors in the network. As seen in FIG. 7, on average, about 2.5 time slots or less are required to find the highest measurement even when a number of sensors is large. For example, the average number of time slots required is about 2.3 for 5 sensors, and increases to about 2.45 when the number of sensors increases to 50. For fewer number of sensors, the average number of time slots required is less. The time can be further reduced if optimizations are used, such as terminating the process when it is determined that a maximum reading cannot exceed an alarm threshold, for example.

As mentioned, on average, about 2.5 time slots or less are required to find the highest measurement. In contrast, a centralized polling algorithm in which a monitor listens to all nodes would require much more time. For example, with 100 sensors, an alarm can be triggered on average within 2.5 time slots using the methods of FIG. 4-6 as opposed to about 50-100 time slots as required by the centralized algorithm.

The methods of FIGS. 4-6 can determine in real-time if secondary action may be required. Because the methods may determine within a handful of time slots whether secondary action is required or not, the central monitoring station may be free to monitor other networks deployed in the environment without sacrificing real-time monitoring rates of any of the sensor networks, for example, or to monitor other parameters such as pressure, temperature, oxygen once monitoring quality of the environment has been completed.

Figure 8:
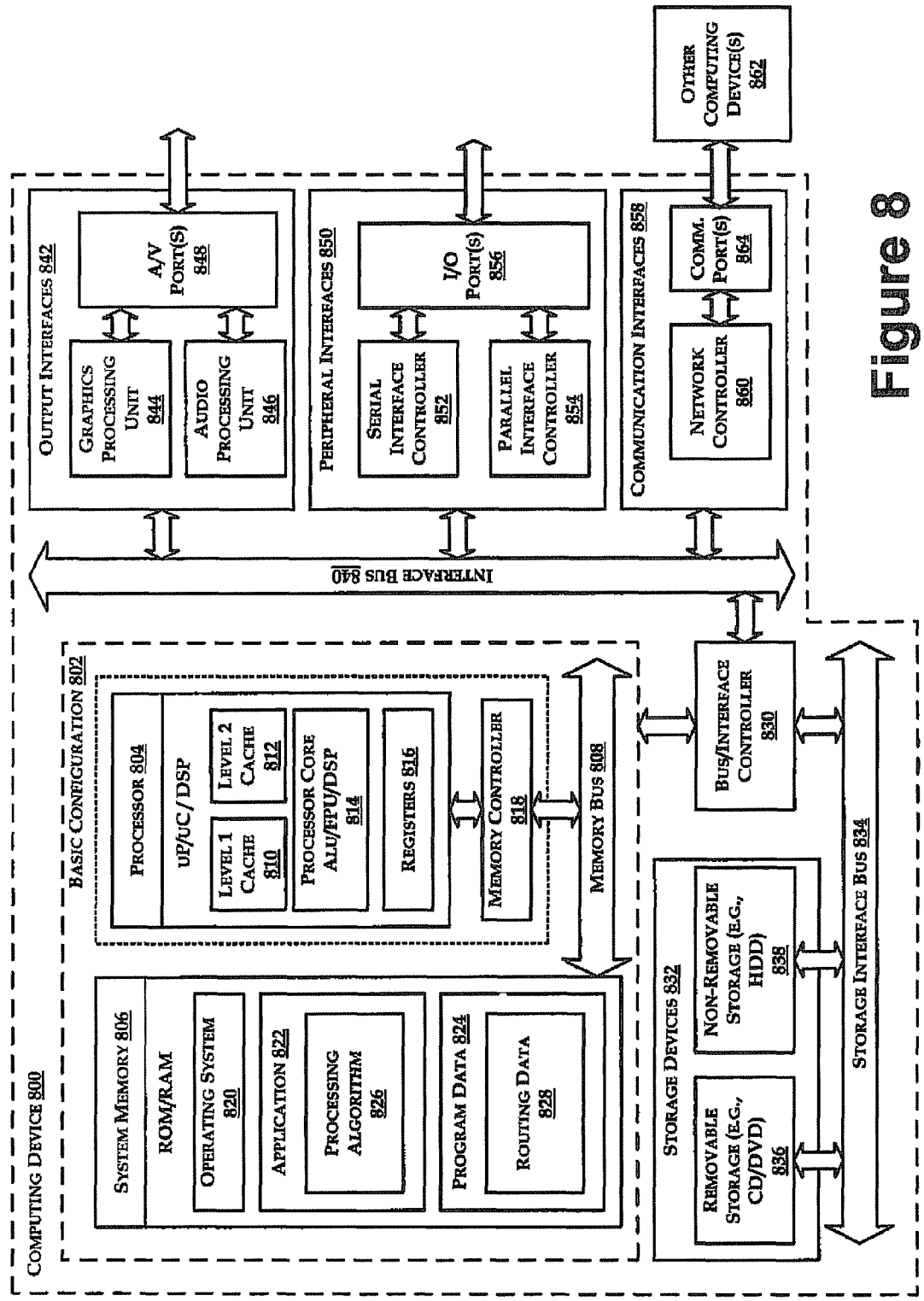
FIG. 8 is a block diagram illustrating an example computing device arranged for sensing characteristics of an environment, or alternatively, arranged as a central monitoring station for receiving signals from sensors in an environment.
Figure 8:
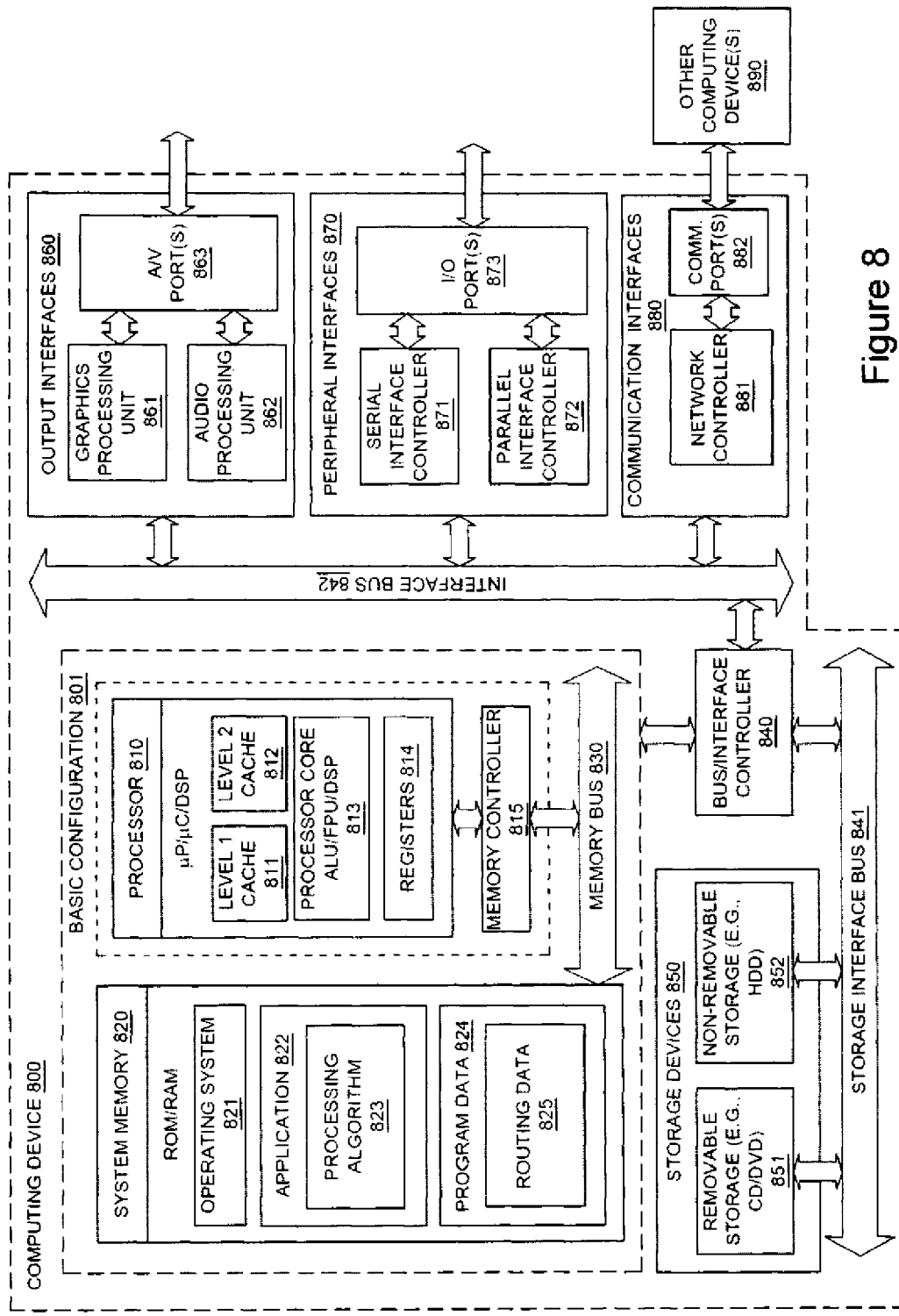

FIG. 8 is a block diagram illustrating an example computing device 800 arranged for sensing characteristics of an environment, or alternatively, arranged as a central monitoring station for receiving signals from sensors in an environment. In a very basic configuration 801, computing device 800 typically includes one or more processors 810 and system memory 820. A memory bus 830 can be used for communicating between the processor 810 and the system memory 820.

Depending on the desired configuration, processor 810 can be of any type including but not limited to a microprocessor (µP), a microcontroller (µC), a digital signal processor (DSP), or any combination thereof. Processor 810 can include one more levels of caching, such as a level one cache 811 and a level two cache 812, a processor core 813, and registers 814. The processor core 813 can include an arithmetic logic unit (ALU), a floating point unit (FPU), a digital signal processing core (DSP Core), or any combination thereof. A memory controller 815 can also be used with the processor 810, or in some implementations the memory controller 815 can be an internal part of the processor 810.

Depending on the desired configuration, the system memory 820 can be of any type including but not limited to volatile memory (such as RAM), non-volatile memory (such as RUM, flash memory, etc.) or any combination thereof. System memory 820 typically includes an operating system 821, one or more applications 822, and program data 824. Application 822 includes algorithms 823 that may be arranged to perform any of the functions shown in FIGS. 4-6, for example, depending on a configuration of the computing device 800. Program Data 824 includes data corresponding to the bits of a received preamble, and bits loaded within an LFSR 825. In some example embodiments, application 822 can be arranged to operate with program data 824 on an operating system 821. This described basic configuration is illustrated in FIG. 8 by those components within dashed line 801.

Computing device 800 can have additional features or functionality, and additional interfaces to facilitate communications between the basic configuration 801 and any required devices and interfaces. For example, a bus/interface controller 840 can be used to facilitate communications between the basic configuration 801 and one or more data storage devices 850 via a storage interface bus 841. The data storage devices 850 can be removable storage devices 851, non-removable storage devices 852, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 820, removable storage 851 and non-removable storage 852 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 800. Any such computer storage media can be part of device 800.

Computing device 800 can also include an interface bus 842 for facilitating communication from various interface devices (e.g., output interfaces, peripheral interfaces, and communication interfaces) to the basic configuration 801 via the bus/interface controller 840. Example output interfaces 860 include a graphics processing unit 861 and an audio processing unit 862, which can be configured to communicate to various external devices such as a display or speakers via one or more A/V ports 863. Example peripheral interfaces 860 include a serial interface controller 871 or a parallel interface controller 872, which can be configured to communicate with external devices such as input devices (e.g., keyboard, mouse, pen, voice input device, touch input device, etc.) or other peripheral devices (e.g., printer, scanner, etc.) via one or more I/O ports 873. An example communication interface 880 includes a network controller 881, which can be arranged to facilitate communications with one or more other computing devices 890 over a network communication via one or more communication ports 882. The communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. The term computer readable media as used herein can include both storage media and communication media.

Computing device 800 can be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 800 can also be implemented as a personal computer including both laptop computer and non-laptop computer configurations.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of transmitting measurements of a sensor, the method comprising:
   receiving a measurement by a sensor unit;
   during a first time slot, transmitting a signal to a monitoring station if the measurement is approximately between a lower and an upper threshold;
   receiving a broadcast from the monitoring station;
   based on the broadcast, updating the lower and the upper threshold for use during a subsequent time slot;
   making a determination whether the updated lower threshold or the updated upper threshold is lower than a minimum value for the lower and upper threshold; and
   based on the determination, performing a subsequent transmission during the subsequent time slot if the measurement is approximately between the updated lower and the updated upper threshold.

2. The method of claim 1, further comprising:
   performing additional subsequent transmissions during subsequent time slots if the measurement is approximately between the updated lower and the updated upper threshold for use during the respective subsequent time slot,
   receiving the broadcast from the monitoring station, and
   based on the broadcast, updating the updated lower and the updated upper threshold until the broadcast from the monitoring station indicates to discontinue transmission.

3. The method of claim 1, wherein, if the updated lower threshold or the updated upper threshold is lower than the minimum value for the lower and upper threshold, performing no subsequent transmission.

4. The method of claim 1, wherein receiving the broadcast from the monitoring station comprises receiving an idle message, and wherein updating the lower threshold comprises decreasing the lower threshold by 1/n, where n is a number of sensors in an environment, wherein the idle message indicates that the monitoring station has not received a sufficient number of signals to make an assessment.

5. The method of claim 1, wherein the signal indicates a magnitude of the measurement.

6. The method of claim 1, wherein the signal indicates that the measurement is within the lower and upper threshold.

7. The method of claim 1, further comprising, at a beginning of the first time slot, calculating the lower and the upper threshold as follows:

$$H_L(k) = \left(1 - \frac{1}{n}\right), \text{ and } H_H(k) = 1$$

where n is a number of sensors in an environment, $H_L(k)$ is the lower threshold at time slot k, and $H_H(k)$ is the upper threshold at time slot k.

8. The method of claim 7, wherein receiving the broadcast from the monitoring station comprises receiving a collision message, wherein the collision message indicates that the monitoring station has received multiple signals from sensors, and wherein updating the lower and the upper threshold comprises increasing the lower threshold and holding the upper threshold substantially constant.

9. The method of claim 8, wherein increasing the lower threshold and holding the upper threshold constant comprises updating the lower and the upper threshold as follows:

$$H_L(k+1) = \frac{(H_L(k) + H_H(k))}{2}, \text{ and } H_H(k+1) = H_H(k).$$

10. The method of claim 7, wherein receiving the broadcast from the monitoring station comprises receiving an idle message, and if no collision has occurred in the past, updating the lower and the upper threshold comprises decreasing the lower and the upper threshold, wherein the idle message indicates that the monitoring station has not received a sufficient number of signals to make an assessment and wherein a collision occurs when the monitoring station has received multiple signals from sensors.

11. The method of claim 10, wherein decreasing the lower and the upper threshold comprises updating the lower and the upper threshold as follows:

$$H_H(k+1) = H_L(k), \text{ and } H_L(k+1) = \left(1 - \frac{(k+1)}{n}\right).$$

12. The method of claim 7, wherein receiving the broadcast from the monitoring station comprises receiving an idle message, and if a collision has occurred in the past, updating the lower and the upper threshold comprises decreasing an interval between the lower and the upper threshold, wherein the idle message indicates that the monitoring station has not received a sufficient number of signals to make an assessment and wherein a collision occurs when the monitoring station has received multiple signals from sensors.

13. The method of claim 12, wherein decreasing the interval between the lower and the upper threshold comprises updating the lower and the upper threshold as follows:

$$H_H(k+1) = H_L(k), \text{ and } H_L(k+1) = H_L(k) - \frac{(H_H(k) - H_L(k))}{2}.$$

14. A method of transmitting measurements of a plurality of sensors within an environment, the method comprising:
   each of the plurality of sensors making a measurement;
   each of the plurality of sensors transmitting a signal to a monitoring station during a time slot when the measurement of the sensor is approximately between a lower and an upper threshold, such that only sensors with measurements between the lower and the upper threshold transmit a signal to the monitoring station;
   each of the plurality of sensors receiving a broadcast from the monitoring station;
   based on the broadcast, each of the plurality of sensors updating the lower and the upper threshold for use during a subsequent time slot;
   each of the plurality of sensors making a determination whether the updated lower threshold or updated upper threshold is lower than a minimum value for the lower and upper threshold; and
   based on the determination, each of the plurality of sensors performing subsequent transmissions during subsequent time slots if the measurement of the sensor is approximately between the updated lower and the updated upper threshold for the respective subsequent time slot, such that over time a lower number of sensors perform subsequent transmissions, wherein if the updated lower threshold or the updated upper threshold is lower than the minimum value for the lower and upper threshold each of the plurality of sensors performing no subsequent transmissions.

15. The method of claim 14, wherein receiving the broadcast from the monitoring station comprises receiving a collision message, wherein the collision message indicates that the monitoring station has received multiple signals from multiple sensors, and wherein updating the lower and the upper threshold for use during a subsequent time slot comprises increasing the lower threshold and holding the upper threshold substantially constant.

16. The method of claim 14, wherein receiving the broadcast from the monitoring station comprises receiving an idle message, and if no collision has occurred in the past, updating the lower and the upper threshold for use during a subsequent time slot comprises decreasing the lower and the upper threshold, wherein the idle message indicates that the monitoring station has not received a sufficient number of signals to make an assessment and wherein a collision occurs when the monitoring station has received multiple signals from multiple sensors.

17. The method of claim 14, wherein receiving the broadcast from the monitoring station comprises receiving a success message, wherein the success message indicates that only about one sensor to about 5% of the plurality of sensors transmitted a signal to the monitoring station.

18. A sensor comprising:
   a sensor unit to obtain measurements of characteristics of an environment;
   a transceiver coupled to the sensor unit to transmit a signal to a monitoring station during a first time slot if the measurement is approximately between a lower and an upper threshold, the transceiver further for receiving a broadcast from the monitoring station; and
   a processing unit coupled to the sensor unit and the transceiver, the processing unit for updating the lower and the upper threshold based on the broadcast received from the monitoring station for use during a subsequent time slot, wherein if the updated lower threshold or the updated upper threshold is lower than a minimum value for the lower and upper threshold, the processing unit directs the transceiver to perform no subsequent transmissions.

19. The sensor of claim 18, wherein the transceiver receives a collision message from the monitoring station, wherein the collision message indicates that the monitoring station has received multiple signals from sensors, and wherein the processing unit updates the lower and the upper threshold by increasing the lower threshold and holding the upper threshold constant.

20. The sensor of claim 18, wherein the transceiver receives an idle message, and if no collision has occurred in the past, the processing unit updates the lower and the upper threshold by decreasing the lower and the upper threshold, wherein the idle message indicates that the monitoring station has not received a sufficient number of signals to make an assessment and wherein a collision occurs when the monitoring station has received multiple signals from sensors.

* * * * *

UNITED STATES PATENT AND TRADEMARK OFFICE
CERTIFICATE OF CORRECTION

Page 1 of 2

PATENT NO. : 8,823,544 B2
APPLICATION NO. : 13/139223
DATED : September 2, 2014
INVENTOR(S) : Mehta It is certified that error appears in the above-identified patent and that said Letters Patent is hereby corrected as shown below:

In the drawings

In Fig. 8, Sheet 7 of 7, delete drawing sheet and insert the attached drawing sheet.

In the specification

In Column 1, Line 10, delete "35 U.S.C. 371" and insert -- 35 U.S.C. § 371 --, therefor.

In Column 6, Line 41, delete "transceiver unit 304" and insert -- transceiver unit 208 --, therefor.

In Column 6, Lines 65-66, delete "central monitoring station 302." and insert -- central monitoring station 300. --, therefor.

In Column 9, Line 23, delete "$u_1$," and insert -- $u_i$, --, therefor.

In Column 14, Line 63, delete "RUM," and insert -- ROM, --, therefor.

In Column 15, Lines 46-47, delete "peripheral interfaces 860" and insert -- peripheral interfaces 870 --, therefor.

Signed and Sealed this
First Day of March, 2016

Michelle K. Lee
*Director of the United States Patent and Trademark Office*